(12) United States Patent
Kugler et al.

(10) Patent No.: US 10,357,261 B2
(45) Date of Patent: Jul. 23, 2019

(54) SINGLE-USE ORTHOPEDIC SURGICAL INSTRUMENT

(71) Applicant: SABIC Global Technologies B.V., Bergen op Zoom (NL)

(72) Inventors: Andrew Kugler, Albany, NY (US); John A. Williams, II, Stevens, PA (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 601 days.

(21) Appl. No.: 15/171,829

(22) Filed: Jun. 2, 2016

(65) Prior Publication Data

US 2017/0245871 A1    Aug. 31, 2017

Related U.S. Application Data

(60) Provisional application No. 62/301,162, filed on Feb. 29, 2016.

(51) Int. Cl.
*A61B 17/17* (2006.01)
*B29C 67/00* (2017.01)
(Continued)

(52) U.S. Cl.
CPC .......... *A61B 17/1764* (2013.01); *A61B 17/15* (2013.01); *A61B 17/155* (2013.01);
(Continued)

(58) Field of Classification Search
CPC ..... A61B 17/17; A61B 17/1764; A61B 17/15; A61B 17/154; A61B 17/155;
(Continued)

(56) References Cited

U.S. PATENT DOCUMENTS

| 5,605,944 A | * | 2/1997 | Heebner | .................... C08J 3/05 523/404 |
| 8,735,773 B2 | | 5/2014 | Lang | |

(Continued)

FOREIGN PATENT DOCUMENTS

| EP | 2856951 A1 | 4/2015 |
| FR | 2910333 A1 | 6/2008 |

(Continued)

OTHER PUBLICATIONS

International Patent Application No. PCT/US2016/035471; Int'l Preliminary Report on Patentability; dated Jun. 1, 2018; 18 pages.
(Continued)

*Primary Examiner* — Christopher J Beccia
(74) *Attorney, Agent, or Firm* — BakerHostetler

(57) ABSTRACT

An orthopedic surgical instrument includes from about 40 wt % to about 85 wt % of a base thermoplastic and from about 15 wt % to about 60 wt % of a filler material. The base thermoplastic includes polyetherimide, polycarbonate, modified polyphenylene ether, polyamide, copolymers of these thermoplastics, and combinations thereof. In some aspects all materials in the orthopedic surgical instrument are biocompatible. An orthopedic surgical kit includes an orthopedic surgical instrument and a container suitable for sealing the orthopedic surgical instrument therein. The orthopedic surgical instrument in the kit includes from about 50 wt % to about 90 wt % of a base thermoplastic selected from the group consisting of polyetherimide, polycarbonate, modified polyphenylene ether, polyamide, copolymers of these thermoplastics, and combinations thereof, and from about 10 wt % to about 50 wt % of a filler material.

18 Claims, 6 Drawing Sheets

(51) Int. Cl.

| | | |
|---|---|---|
| *A61L 31/04* | (2006.01) | |
| *B29C 45/00* | (2006.01) | |
| *A61B 17/15* | (2006.01) | |
| *B29C 64/00* | (2017.01) | |
| *B29C 64/386* | (2017.01) | |
| *A61B 17/00* | (2006.01) | |
| *B29K 105/16* | (2006.01) | |
| *B29L 31/00* | (2006.01) | |
| *B33Y 80/00* | (2015.01) | |
| *A61B 34/10* | (2016.01) | |

(52) U.S. Cl.
CPC .......... *A61B 17/17* (2013.01); *B29C 45/0001* (2013.01); *B29C 64/00* (2017.08); *B29C 64/386* (2017.08); *A61B 2017/0023* (2013.01); *A61B 2017/00526* (2013.01); *A61B 2017/00853* (2013.01); *A61B 2017/00955* (2013.01); *A61B 2034/108* (2016.02); *A61L 2400/10* (2013.01); *B29K 2105/16* (2013.01); *B29L 2031/7546* (2013.01); *B33Y 80/00* (2014.12)

(58) Field of Classification Search
CPC .......... A61B 2017/00955; A61B 2017/00526; A61B 2017/00853; A61B 2017/0023; A61B 2034/108; A61L 31/041; A61L 31/14; A61L 2400/10; B29C 45/0001; B29C 64/386; B29C 64/00; B29K 2105/16; B29L 2031/7546; B33Y 80/00
See application file for complete search history.

(56) References Cited

U.S. PATENT DOCUMENTS

| | | | |
|---|---|---|---|
| 8,933,170 B2* | 1/2015 | Parakkal | C08L 69/00 |
| | | | 525/88 |
| 9,072,531 B2 | 7/2015 | Fitz et al. | |
| 2011/0071572 A1 | 3/2011 | Sixto et al. | |
| 2014/0208578 A1* | 7/2014 | Linderman | A61F 2/30756 |
| | | | 29/592 |
| 2014/0230215 A1 | 8/2014 | Van den Broeck et al. | |
| 2015/0366677 A1* | 12/2015 | Porzel | B29C 43/006 |
| | | | 623/20.35 |

FOREIGN PATENT DOCUMENTS

| | | |
|---|---|---|
| WO | 200167970 A1 | 9/2001 |
| WO | 2007008667 A1 | 1/2007 |
| WO | 2014095853 A1 | 6/2014 |
| WO | 2014140808 A1 | 9/2014 |
| WO | 2015112566 A1 | 7/2015 |

OTHER PUBLICATIONS

International Patent Application No. PCT/US2016/035497; Int'l Preliminary Report on Patentability; dated Sep. 13, 2018; 8 pages.
International Patent Application No. PCT/US2016/035491; Int'l Preliminary Report on Patentability; dated Sep. 13, 2018; 9 pages.

* cited by examiner

SINGLE-USE ORTHOPEDIC SURGICAL INSTRUMENT

RELATED APPLICATION

The present application claims the benefit of U.S. Provisional Application No. 62/301,162, filed Feb. 29, 2016, the contents of which are incorporated herein by this reference in its entirety.

FIELD OF THE DISCLOSURE

The present disclosure relates to surgical instruments, and in particular to surgical instruments and methods for making surgical instruments that include a base thermoplastic and a filler material.

BACKGROUND OF THE DISCLOSURE

Instruments currently used in surgical procedures, and in particular arthroplasty procedures such as knee replacement procedures, are typically made out of metal and are reusable. In addition, implant trials are also often reusable and formed of metal or plastic. In a typical knee replacement surgery, there are a large number (up to 8-10) trays filled with hundreds of instruments and trials. After a surgery, each of these individual devices must be cleaned, maintained (i.e., sharpened, checked for damage, etc.), sterilized, and tracked. The instruments and associated logistics relating to cleaning, maintenance, storage and tracking of these instruments are costly, and impose a major burden on the hospital. In addition, if cleaning and sterilization are not performed perfectly, hospital-acquired infections can occur. By utilizing new designs and consolidating parts—made possible through the use of advanced plastic materials and injection molding processes—it has been possible to reduce the number of instruments and the total number of trays to approximately 2-6. This has drastically reduced the reprocessing, sterilization, storage and tracking requirements for these instruments.

For knee replacement surgery, cutting guides are used to remove bone and allow a good fit with the artificial joint implant components. Cutting guides provide for alignment and fit of the joint and are important to good surgical outcomes (i.e., minimizing pain, improving ease of walking, reducing the need for subsequent procedures, etc.). Standard cutting guides, however, are made from metal materials that are designed to be reused and are costly. As a result, they need to be thoroughly cleaned and sterilized. This often requires disassembly and can be problematic due to the many crevices and other areas where biological material can be lodged.

Personalized cutting guides for use in knee arthroplasty procedures have been made from unfilled nylon 12. These cutting guides have less than desired strength and stiffness, however, which can lead to imprecise cuts and wear debris contaminating the surgical site, and which can present an infection hazard. Some personalized cutting guides use metal inserts on cutting surfaces to prevent wear. Metal inserts add significant cost and increase the manufacturing complexity, however.

These and other shortcomings are addressed by aspects of the present disclosure.

BRIEF DESCRIPTION OF THE FIGURES

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

SUMMARY

Figure 2:
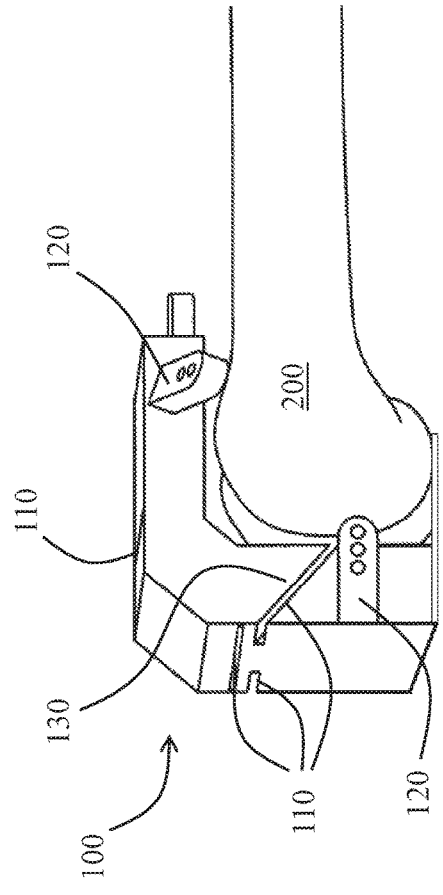
FIG. 2 is a side perspective view of the surgical instrument of FIG. 1.

Aspects of the disclosure relate to an orthopedic surgical instrument including from about 40 wt % to about 85 wt % of a base thermoplastic selected from the group consisting of polyetherimide, polycarbonate, modified polyphenylene ether, polyamide, copolymers of these thermoplastics, and combinations thereof and from about 15 wt % to about 60 wt % of a filler material. In some aspects all materials in the orthopedic surgical instrument are biocompatible.

Aspects of the disclosure also relate to an orthopedic surgical kit including an orthopedic surgical instrument and a container suitable for sealing the orthopedic surgical instrument therein. The orthopedic surgical instrument includes from about 50 wt % to about 90 wt % of a base thermoplastic selected from the group consisting of polyetherimide, polycarbonate, modified polyphenylene ether, polyamide, copolymers of these thermoplastics, and combinations thereof and from about 10 wt % to about 50 wt % of a filler material. In some aspects all materials in the orthopedic surgical instrument are biocompatible.

In a further aspect of the disclosure a method for making an orthopedic surgical instrument includes forming the orthopedic surgical instrument from a resin composition comprising from about 50 wt % to about 90 wt % of a base thermoplastic and from about 10 wt % to about 50 wt % of a filler material. The base thermoplastic is selected from the group consisting of polyetherimide, polycarbonate, modified polyphenylene ether, polyamide, copolymers of these thermoplastics, and combinations thereof. In some aspects all materials in the orthopedic surgical instrument are biocompatible.

DETAILED DESCRIPTION

The present disclosure can be understood more readily by reference to the following detailed description of the disclosure and the Examples included therein. In various aspects, the present disclosure pertains to an orthopedic surgical instrument, including from about 40 wt % to about 85 wt % of a base thermoplastic and from about 15 wt % to about 60 wt % of a filler material. The base thermoplastic includes polyetherimide, polycarbonate, modified polyphenylene ether, polyamide, copolymers of these thermoplastics, and combinations thereof. In some aspects all materials in the orthopedic surgical instrument are biocompatible.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting.

Various combinations of elements of this disclosure are encompassed by this disclosure, e.g., combinations of elements from dependent claims that depend upon the same independent claim.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

All publications mentioned herein are incorporated herein by reference to disclose and describe the methods and/or materials in connection with which the publications are cited.

Definitions

It is also to be understood that the terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a polycarbonate" includes mixtures of two or more polycarbonate polymers.

As used herein, the term "combination" is inclusive of blends, mixtures, alloys, reaction products, and the like.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optional lubricant material" means that the lubricant material can or cannot be included and the description includes surgical instruments that both include and do not include a lubricant material.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The terms "BisA," "BPA," or "bisphenol A," which can be used interchangeably, as used herein refers to a compound having a structure represented by the formula:

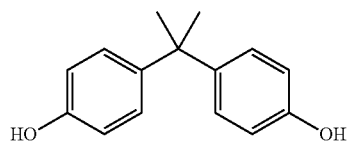 [SMILES: CC(C)(c1ccc(O)cc1)c1ccc(O)cc1]

BisA can also be referred to by the name 4,4'-(propane-2,2-diyl)diphenol; p,p'-isopropylidenebisphenol; or 2,2-bis(4-hydroxyphenyl)propane. BisA has the CAS #80-05-7.

As used herein, "polycarbonate" refers to an oligomer or polymer comprising residues of one or more dihydroxy compounds, e.g., dihydroxy aromatic compounds, joined by carbonate linkages; it also encompasses homopolycarbonates, copolycarbonates, and (co)polyester carbonates.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Certain abbreviations are defined as follows: "g" is grams, "kg" is kilograms, "° C." is degrees Celsius, "min" is minutes, "mm" is millimeter, "mPa" is megapascal, "WiFi" is a system of accessing the internet from remote machines, "GPS" is Global Positioning System—a global system of U.S. navigational satellites which provide positional and velocity data. "LED" is light-emitting diode, "RF" is radio frequency, and "RFID" is radio frequency identification.

Unless otherwise stated to the contrary herein, all test standards are the most recent standard in effect at the time of filing this application.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions and it is understood that there are a variety of structures that can perform the same function that are related to the disclosed structures, and that these structures will typically achieve the same result.

Surgical Instrument

Aspects of the disclosure relate to a surgical instrument, and in particular an orthopedic surgical instrument, including from about 40 wt % to about 85 wt % of a base thermoplastic and from about 15 wt % to about 60 wt % of a filler material. In certain aspects the base thermoplastic includes polyetherimide, polycarbonate, modified polyphenylene ether, polyamide, copolymers of these thermoplastics, and combinations of these polymers. The materials in the orthopedic surgical instrument and/or the surgical instrument may satisfy one or more standards for biocompatibility of medical devices. One exemplary standard is ISO 10993-1:2009, "Biological evaluation of medical devices—Part 1: Evaluation and testing within a risk management process."

The filler material may be selected to provide one or more desirable properties to the surgical instrument, such as but not limited to surface hardness and strength. Exemplary filler materials that may be used in aspects of the disclosure include, but are not limited to, carbon, ultra-high molecular weight polyethylene ("UHMWPE"), and combinations thereof. In certain aspects, the surgical instrument includes from about 15 wt % to about 40 wt % of the filler material, or from about 15 wt % to about 30 wt % of the filler material, or from about 20 wt % to about 40 wt % of the filler material. The filler material can be included in the surgical instrument in any form, including but not limited to fiber (e.g., carbon fiber or UHMWPE fiber) form or nanotube (e.g., carbon nanotube) form.

A lubricant material may optionally be added to the surgical instrument to minimize wear of the surgical instrument during use, which could result in undesirable generation of debris. In some aspects up to 20 wt % of the lubricant material is included in the surgical instrument, or up to 15 wt %, or up to 10 wt %, or even up to 5 wt % of the lubricant material. Exemplary lubricant materials that may be suitable for use in aspects of the disclosure include, but are not limited to, polytetrafluoroethylene, polyfluoropolyether, hydrocarbon-based synthetic oils, graphite, titanium dioxide, molybdenum disulfide, boron nitride, silicone compounds, and combinations thereof. A particularly suitable silicone compound may include a biocompatible silicone elastomer. Other biocompatible blends of elastomers and/or thermoplastic polymers can also be used. The lubricant material may be a synthetic oil and/or a solid lubricant. Exemplary synthetic oil lubricants include but are not limited to polyfluoropolyether (PFPE) synthetic oils, polytetrafluoroethylene (PTFE) synthetic oils, and hydrocarbon-based synthetic oils (including co-oligomers of ethylene and olefins). Exemplary solid lubricants include low molecular weight polytetrafluoroethylene powders, titanium dioxide micropowders, molybdenum disulfide micropowders, graphite micropowders or flakes, and boron nitride micropowders.

In addition to the foregoing components, the disclosed surgical instrument can optionally include an effective amount of one or more additional additive materials ordinarily incorporated in thermoplastic materials of this type, with the proviso that the additives are selected so as to not significantly adversely affect the desired properties of the surgical instrument. Combinations of additives can be used. Such additives can be combined with the other components at a suitable time during the mixing of the components prior to or during formation. Exemplary and non-limiting examples of additive materials that can be present in the disclosed surgical instrument include additional reinforcing fillers, an acid scavenger, anti-drip agent, antioxidant, antistatic agent, chain extender, colorant (e.g., pigment and/or dye), de-molding agent, flow promoter, lubricant, mold release agent, plasticizer, quenching agent, flame retardant stabilizer (including for example a thermal stabilizer, a hydrolytic stabilizer, or a light stabilizer), UV reflecting additive, or any combination thereof.

In a particular aspect, the orthopedic surgical instrument includes about 60 wt % to about 80 wt % base thermoplastic including polyetherimide, polycarbonate or polyamide, and about 20 wt % to about 40 wt % filler material including carbon.

In another particular aspect, the orthopedic surgical instrument includes about 55 wt % to about 80 wt % base thermoplastic including polyetherimide, polycarbonate or polyamide, about 15 wt % to about 30 wt % filler material including carbon, and about 5 wt % to about 15 wt % of a lubricant material.

In a further particular aspect, the orthopedic surgical instrument includes about 60 wt % to about 80 wt % base thermoplastic and about 20 wt % to about 40 wt % filler material including ultra-high molecular weight polyethylene.

Figure 1:
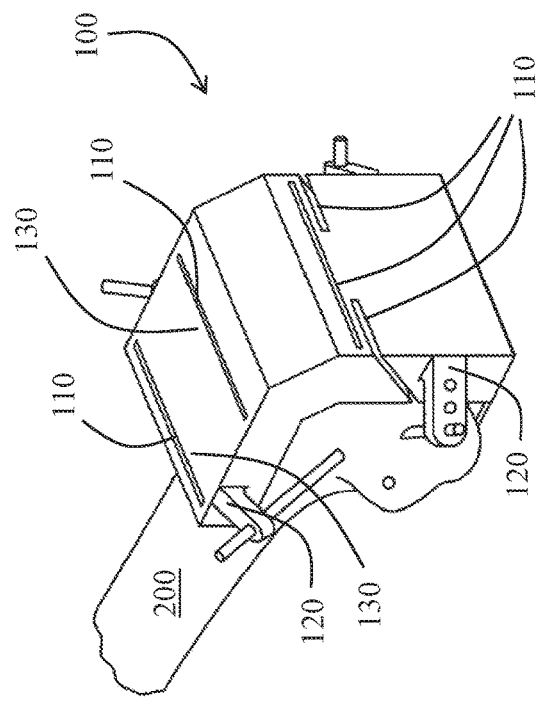
FIG. 1 is a top perspective view of a surgical instrument according to an aspect of the disclosure.

The orthopedic surgical instrument according to aspects of the disclosure may be useful in various surgical applications. In one aspect such as that illustrated in FIGS. 1 and 2, the orthopedic surgical instrument may be a cutting guide 100. A cutting guide is used in joint replacement surgery to assist the surgeon in properly aligning the cutting implement (saw, drill, etc.) to the bone surrounding the joint to be replaced so that the bone can be cut and prepared to receive the joint implant(s). The cutting guide 100 includes a plurality of slots 110 for receiving the cutting implement (not illustrated) and brackets 120 for removably securing the cutting guide 100 to the bone 200. Further, although not illustrated, the cutting guide 100 may include through holes or other securing features for securing the cutting guide 100 to the bone 200.

In certain aspects the cutting guide 100 includes at least one first surface 130 proximate a location to where a cutting implement is adjacent the cutting guide during use. During formation of the surgical instrument (e.g., cutting guide 100), the temperature of the at least one surface 130 may be controlled relative to the temperature of the rest of the surgical instrument such that predominantly more of one of or more of the materials in the surgical instrument is located near, at or on the at least one surface 130 than at other surfaces of the surgical instrument. Controlling the temperatures of the at least one surface 130 relative to other surfaces of the surgical instrument during formation can cause targeted migration of one or more of the materials in the surgical instrument towards or away from the at least one surface 130, resulted in targeted properties at the at least one surface 130. For example, in one aspect during formation of the surgical instrument (e.g., cutting guide 100), the temperature of the at least one surface 130 may be controlled relative to the temperature of the rest of the surgical instrument such that predominantly more of the filler material in the surgical instrument is located near, at or on the at least one surface 130 than at other surfaces of the surgical instrument. In another aspect, during formation of the surgical instrument (e.g., cutting guide 100), the temperature of the at least one surface 130 may be controlled relative to the temperature of the rest of the surgical instrument such that predominantly more of the base thermoplastic in the surgical instrument is located near, at or on the at least one surface 130 than at other surfaces of the surgical instrument. In a certain aspect, during formation of the surgical instrument (e.g., cutting guide 100), the temperature of the at least one surface 130 may be controlled relative to the temperature of the rest of the surgical instrument such that predominantly more of the lubricant in the surgical instrument is located near, at or on the at least one surface 130 than at other surfaces of the surgical instrument.

In some aspects of the present disclosure the surgical instruments do not include any secondary surface enhancements and/or are uncoated on at least one surface. As used herein, secondary surface enhancements include, but are not limited to, coating, plating, plasma treatment, assembly, painting, polishing, milling, and drilling operations that strengthen and/or harden the surface of the surgical instrument or the instrument itself and allow it to be used in surgical applications. Secondary surface enhancements do not, however, include cleaning and/or sterilization processes that are applied to the surgical instrument following manufacture or use. Moreover, secondary surface enhancements do not include packaging processes applied to the surgical instrument to prepare the surgical instrument for transportation/storage/etc.

In certain aspects, the at least one surface is the surface that is proximate a cutting implement. Purely by way of example, in an aspect in which the surgical instrument is a cutting guide 100, the at least one surface 130 may be uncoated or may not include any secondary surface enhancements. In other words, the materials included in the cutting guide 100 and described herein result in the surgical instrument/cutting guide 100 having sufficient surface hardness and/or strength such that additional coatings or secondary surface enhancements are not necessary for the instrument to be used in surgical applications, and in particular cutting applications. In further aspects, the method by which the surgical instrument/cutting guide 100 is formed (described above) that result in the at least one surface 130 having predominantly more of one of or more of the materials in the surgical instrument located near, at or on the at least one surface 130 than at other surfaces of the surgical instrument, provide the at least one surface with sufficient surface hardness and/or strength such that additional coatings or secondary surface enhancements are not necessary for the instrument to be used in surgical applications, and in particular cutting applications.

Surgical instruments according to aspects of the disclosure may have improved surface hardness and/or strength as compared to surgical instruments formed from previously known polymeric materials such as polyamide-12 (Nylon 12), which may be prone to scratching and/or debris generation. Accordingly, surgical instruments according to some aspects of the disclosure exhibit minimal scratching during use, particularly during cutting operations. For example, in some aspects where the surgical instrument is a cutting guide, the cutting implement (e.g., a cutting saw, drill, etc.) will cause minimal scratching to surfaces of the cutting guide proximate the cutting implement during use. In certain aspects, minimal scratching may be considered to be a small enough amount of scratching so as not to cause observable debris generation from the surface of the surgical instrument during use.

In other aspects, surgical instruments according to the disclosure exhibit no observable debris generation during use, particularly during cutting operations. For example, in aspects where the surgical instrument is a cutting guide, the cutting implement will cause no observable debris generation from surfaces of the cutting guide proximate the cutting implement during use. This ensures good alignment of cutting implements (e.g., saws, drills, etc.) and reduces or minimizes the risk of contamination of the surgical site from foreign material.

The surgical instrument according to some aspects of the disclosure is a single-use instrument. Thus, in contrast to prior surgical instruments which may be made from metal and which must be sterilized, packaged and stored for re-used, the surgical instrument, because it can be made economically from the polymeric and other materials described herein, may be used on one patient during one surgical procedure and then discarded.

Methods for Making a Surgical Instrument

Aspects of the disclosure also relate to methods for making a surgical instrument, including forming the surgical instrument from a resin composition, the resin composition including from about 50 wt % to about 90 wt % of a base thermoplastic and from about 10 wt % to about 50 wt % of a filler material. In some aspects the base thermoplastic may include polyetherimide, polycarbonate, modified polyphenylene ether, polyamide, copolymers of these thermoplastics, and combinations thereof. In further aspects the materials in the surgical instrument may satisfy one or more standards for biocompatibility of medical devices. One exemplary standard is ISO 10993-1:2009, "Biological evaluation of medical devices—Part 1: Evaluation and testing within a risk management process."

In some aspects the resin composition may further include up to 20 wt % of a lubricant material. Exemplary materials for the lubricant material and filler material are described above and not duplicated here.

In addition to the foregoing components, the disclosed resin composition can optionally include an effective amount of one or more additional additive materials ordinarily incorporated in resin compositions of this type, with the proviso that the additives are selected so as to not significantly adversely affect the desired properties of the resin composition and/or the resulting surgical instrument. Combinations of additives can be used. Such additives can be combined with the other components at a suitable time during the mixing of the components prior to or during formation. Exemplary and non-limiting examples of additive materials are that can be present in the disclosed resin composition include additional reinforcing fillers, an acid scavenger, anti-drip agent, antioxidant, antistatic agent, chain extender, colorant (e.g., pigment and/or dye), de-molding agent, flow promoter, lubricant, mold release agent, plasticizer, quenching agent, flame retardant stabilizer (including for example a thermal stabilizer, a hydrolytic stabilizer, or a light stabilizer), UV reflecting additive, or any combination thereof.

Figure 3:
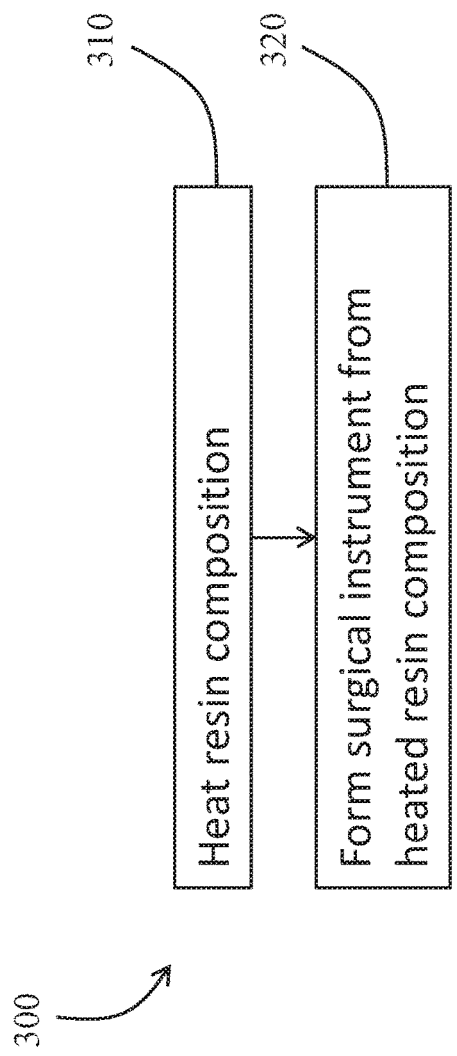
FIG. 3 is a flowchart illustrating a method according to an aspect of the disclosure.

With reference to FIG. 3, aspects of a method for forming a surgical instrument 300 are further described by steps of heating the resin composition 310 and forming the surgical instrument from the heated resin composition 320. As described above, the resin composition may include from about 50 wt % to about 90 wt % of a base thermoplastic and from about 10 wt % to about 50 wt % of a filler material. The step of forming the surgical instrument from the heated resin composition 320 may be performed by any suitable process. In one aspect, the surgical instrument is injection molded from the heated resin composition. In another aspect, the surgical instrument is formed from the heated resin composition in an additive manufacturing process. Exemplary additive manufacturing processes include, but are not limited to, three-dimensional printing processes, laser sintering processes (e.g., selective laser sintering, "SLS"), laser melting processes (e.g., selective laser melting, "SLM"), and fused deposition modeling ("FDM") processes.

Figure 4:
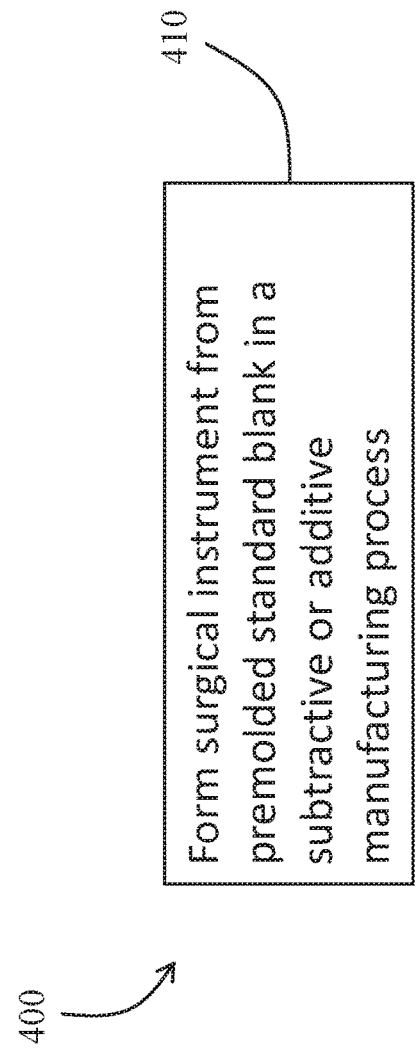
FIG. 4 is a flowchart illustrating a method according to another aspect of the disclosure.

In a further aspect of the method illustrated with reference to FIG. 4, the surgical instrument is formed from a premolded standard blank in a subtractive or additive manufacturing process 410. A subtractive manufacturing process is one in which material is removed from the premolded standard blank to form the surgical instrument. Material may be removed by any suitable method, including but not limited to stamping, cutting, grinding, settling, filtering, and flaring. Subtractive manufacturing may, in some aspects, offer advantages over other manufacturing methods, such as good dimensional control and surface finish of the surgical instrument, a high degree of repeatability for end-use manufacture, and the ability to use a wide range of base thermoplastics in the premolded standard blank. Additive manufacturing processes are described above.

The premolded standard blank may include the resin composition according to aspects described herein. The premolded standard blank may be in any suitable form, such as but not limited to a rectangular, square, cylindrical, or disc-shaped block, and/or any form that is selected or designed to minimize the amount of personalization required for a particular additive or subtractive manufacturing process. The premolded standard blank may be solid or it may have voids/cavities. It will be recognized that the premolded standard blank will need to be larger than the surgical instrument to be formed in at least one dimension if it will be used in a subtractive manufacturing process. A person skilled in the art can select a premolded standard blank of suitable size, shape and configuration for a particular surgical instrument to be formed.

In certain aspects, methods for forming the surgical instrument may include controlling a temperature of at least one surface of the instrument proximate a location to where a cutting implement is adjacent the surgical instrument during use such that predominantly more of one or more of the materials in the resin composition is located near, at or on the at least one first surface of the surgical instrument than at other surfaces of the surgical instrument. Such methods are described above and not duplicated here.

In certain aspects of the method no secondary surface enhancements are performed on the at least one surface. In further aspects the surgical instrument formed according to the described methods is sterilized and/or packaged.

Surgical Kit

Aspects of the present disclosure also relate to an surgical kit, including a surgical instrument such as an orthopedic surgical instrument and a container suitable for sealing the surgical instrument therein. The surgical instrument includes from about 50 wt % to about 90 wt % of a base thermoplastic, and from about 10 wt % to about 50 wt % of a filler material. In certain aspects the base thermoplastic includes polyetherimide, polycarbonate, modified polyphenylene ether, polyamide, copolymers of these thermoplastics, and combinations thereof. The materials in the orthopedic surgical instrument and/or the surgical instrument may satisfy one or more standards for biocompatibility of medical devices. One exemplary standard is ISO 10993-1:2009, "Biological evaluation of medical devices—Part 1: Evaluation and testing within a risk management process."

In one aspect, the container includes one or more materials suitable for maintaining sterility of the surgical instrument contained therein during transportation or storage thereof. In particular aspects, the one or more materials include high density polyethylene, polyester, polyethylene, polycarbonate, polyurethane, polyethylene terephthalate glycol, polyethylene terephthalate, acrylonitrile-butadiene-styrene, polyvinyl chloride, polystyrene, cellophane, laminates of one or more of these materials, coextruded films including one or more of these materials, and combinations thereof. Particularly suitable container materials include, but are not limited to, nonwoven high density polyethylene such as Tyvek™ (available from DuPont), thermoplastic polyurethane film (TPU), polyethylene terephthalate glycol-modified (PETG), polyethylene terephthalate (PETE), and acrylonitrile-butadiene-styrene (ABS).

Method for Making a Customized Surgical Instrument

Figure 5:
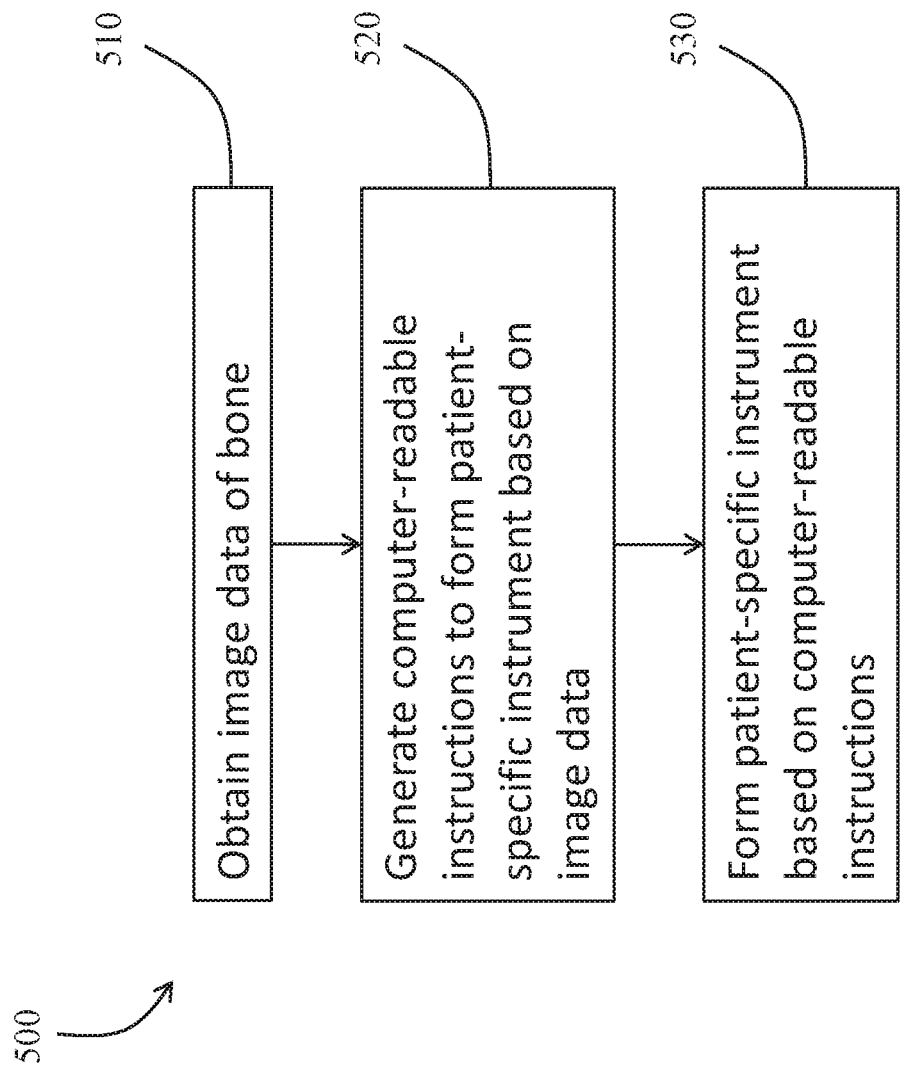
FIG. 5 is a flowchart illustrating a method according to a further aspect of the disclosure.

Aspects of the present disclosure further relate to methods for making a customized surgical instrument, such as a customized orthopedic surgical instrument, for use in repairing a joint of a patient. With reference to FIG. 5, the method includes obtaining image data associated with at least a portion of a bone corresponding to the joint of the patient at 510, generating computer-readable instructions to form a patient-specific surgical instrument based at least in part on the image data at 520, and forming the patient-specific surgical instrument based on the computer-readable instructions at 530. The patient-specific surgical instrument includes a resin composition, the resin composition including from about 50 wt % to about 90 wt % of a base thermoplastic and from about 10 wt % to about 50 wt % of a filler material. The base thermoplastic and filler material may include materials such as those described herein. In certain aspects the surgical instrument includes at least one surface portion having a shape that substantially conforms to a corresponding surface portion of the bone. In further aspects all materials in the orthopedic surgical instrument are biocompatible.

At step 510 image data may be obtained of at least a portion of a bone corresponding to a joint of a patient. The image can be, for example, an intraoperative image including that acquired from a surface detection method using any techniques known in the art, e.g., mechanical, optical, ultrasound, and known devices such as MRI, CT, ultrasound, digital tomofsynthesis and/or optical coherence tomography images. In any of the aspects described herein, the joint can be a knee, shoulder, hip, vertebrae, elbow, ankle, wrist, etc.

At step 520 computer-readable instructions are generated to form a patient-specific surgical instrument based at least in part on the image data. The computer-readable instructions may be generated by a computer system, and may include, e.g., schematics, diagrams, specifications or other data that would allow a manufacturing system, such as an additive manufacturing system or a subtractive manufacturing to form the surgical instrument. The computer-readable instructions may include standard information that is known in the art, and in some aspects are provided as a 3D computer-aided design (CAD) stereolithography (STL) file format or 2D CAD file which may be converted into an STL file format. Exemplary additive manufacturing systems include those discussed above, and are not duplicated here.

At step 530 the patient-specific surgical instrument is formed based on the computer-readable instructions generated at step 520. The patient-specific surgical instrument includes the resin composition described herein, and includes from about 50 wt % to about 90 wt % of a base thermoplastic and from about 10 wt % to about 50 wt % of a filler material, the contents of each of which is described herein. The patient-specific surgical instrument may be formed by any process described herein, including but not limited to an injection molding process, an additive manufacturing process, or it may be subtractively molded from a premolded standard blank in a subtractive molding process. Exemplary additive manufacturing processes include those discussed above, and are not duplicated here. In certain aspects the surgical instrument includes at least one surface portion having a shape that substantially conforms to a corresponding surface portion of the bone. The surgical instrument in such aspects would thus include at least one surface that is substantially a negative of, a mirror image of and/or conforms to at least one surface of the bone.

It will be recognized that some operator input and/or interaction may occur at some or all of steps 510, 520 and 530.

Other aspects of the surgical instrument and methods for making it, including the quantities and types of materials in the resin composition and/or surgical instrument, features of the surgical instrument, and properties of the surgical instrument are discussed above and not reproduced here.

Patient-Specific Surgical Instrument

Aspects of the disclosure also relate to a patient-specific surgical instrument, such as an orthopedic surgical instrument, for use in repairing a joint of a patient, the surgical instrument including from about 50 wt % to about 90 wt % of a base thermoplastic and from about 10 wt % to about 50 wt % of a filler material. The patient-specific surgical instrument includes at least one surface portion having a shape that substantially conforms to a corresponding surface portion of a bone corresponding to the joint of the patient. In some aspects all materials in the patient-specific surgical instrument are biocompatible. The base thermoplastic may include polyetherimide, polycarbonate, modified polyphenylene ether, polyamide, copolymers of these thermoplastics, and combinations thereof.

Figure 6:
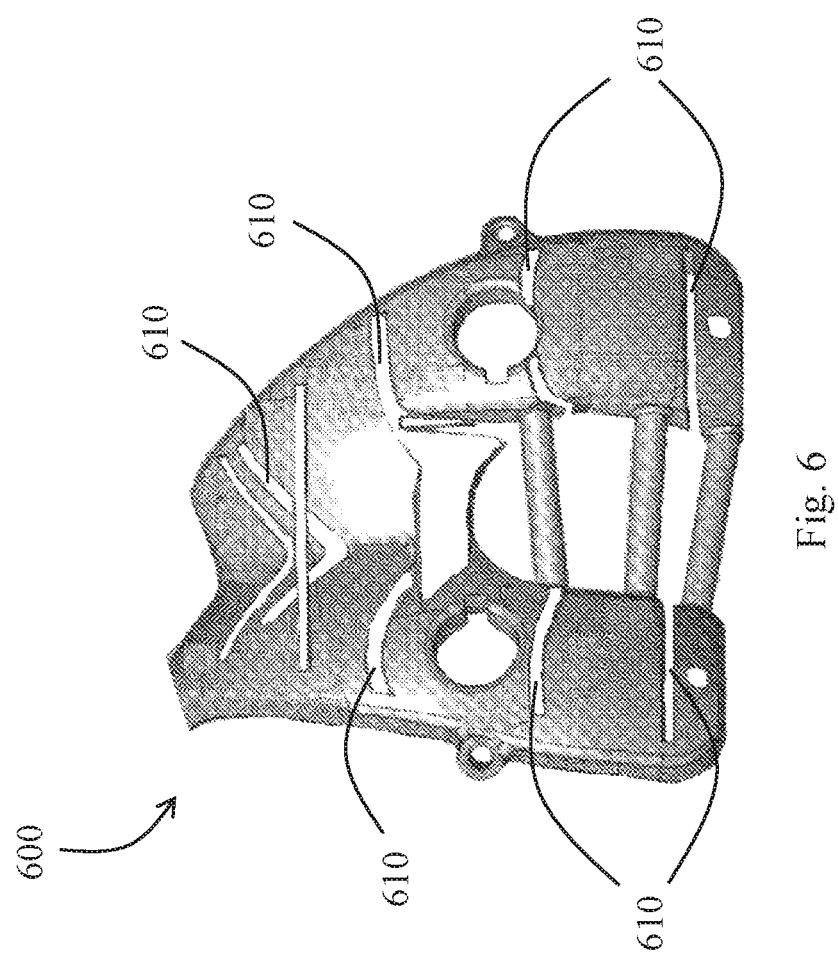
FIG. 6 is a front perspective view of a customized surgical instrument according to an aspect of the disclosure.

In one particular aspect illustrated in FIG. 6, the patient-specific surgical instrument is a cutting guide 600. The cutting guide 600 includes a plurality of guide slots 610 for various incisions that may need to be made during a joint (e.g., knee) replacement procedure. The cutting guide 600 is customized, having a shape that substantially conforms to the surface portion of the bone to be cut. In this manner, the cutting guide 600 conforms to the bone, which helps to ensure proper alignment of the cutting implement (e.g., cutting saw, drill, etc.) with the bone to be cut. Customization also allows the cutting guide 600 to be attached to the bone with less attachment points, resulting in less blood loss, a faster surgical procedure and better surgical outcomes. Further, customization allows for the manufacture of a smaller surgical instrument with less material, minimizing waste and reducing cost.

Other aspects of the surgical instrument and methods for making it, including the quantities and types of materials in the resin composition and/or surgical instrument, features of the surgical instrument, and properties of the surgical instrument are discussed above and not reproduced here.

System for Manufacture of a Personalized Surgical Instrument

Figure 7:
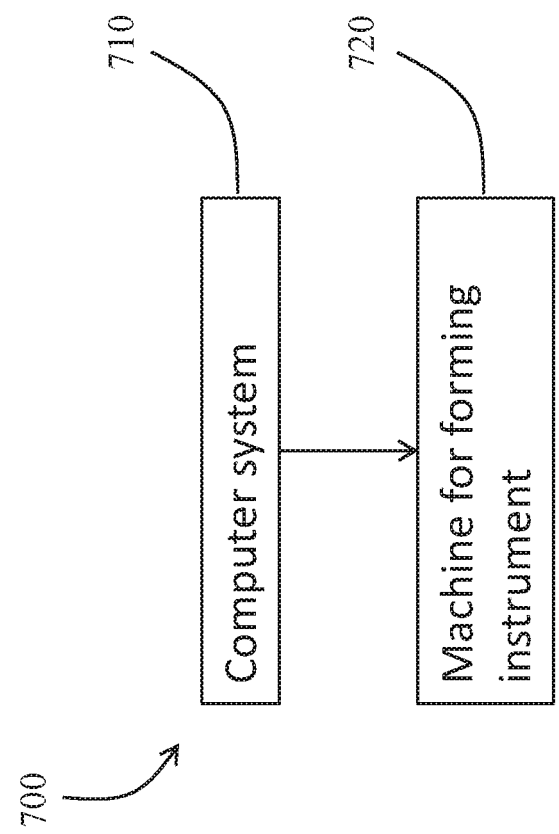
FIG. 7 is a flowchart illustrating a system according to an aspect of the disclosure.

With reference to FIG. 7, aspects of the disclosure further relate to a system 700 for making a customized surgical instrument, such as an orthopedic surgical instrument, for use in repairing a joint of a patient. The system 700 includes a computer system 710 for generating computer-readable instructions to form a patient-specific surgical instrument based at least in part on image data obtained from at least a portion of a bone corresponding to the joint of the patient, and a machine 720 for forming a patient-specific surgical instrument from the computer-readable instructions. The patient-specific surgical instrument includes a resin composition, the resin composition including from about 50 wt % to about 90 wt % of a base thermoplastic, and from about 10 wt % to about 50 wt % of a filler material. The patient-specific surgical instrument includes at least one surface portion having a shape that substantially conforms to a corresponding surface portion of the bone. In some aspects all materials in the patient-specific surgical instrument are biocompatible.

The computer system 710 generates computer-readable instructions to form a patient-specific surgical instrument based at least in part on image data obtained from at least a portion of a bone corresponding to the joint of the patient. The image data may be obtained by a surface detection method using any techniques known in the art, e.g., mechanical, optical, ultrasound, and known devices such as MRI, CT, ultrasound, digital tomofsynthesis and/or optical coherence tomography images.

The computer-readable instructions include, e.g., schematics, diagrams, specifications or other data that will allow the machine 720 to form the patient-specific surgical instrument from the computer-readable instructions. The computer-readable instructions may include standard information that is known in the art, and in some aspects are provided as a 3D computer-aided design (CAD) stereolithography (STL) file format or 2D CAD file which may be converted into an STL file format.

The machine 720 forms the patient-specific surgical instrument from the computer-readable instructions provided by the computer system 710. The machine 720 can be any suitable apparatus for forming the surgical instrument, including but not limited to an additive manufacturing apparatus or a subtractive manufacturing apparatus. Examples of suitable additive manufacturing apparatuses include, but are not limited to, a three-dimensional printing apparatus, a laser sintering apparatus, a laser melting apparatus, and a fused deposition modeling apparatus.

It will be recognized that some operator input and/or interaction may occur during operation of the computer system 710 and/or machine 720.

As discussed, in certain aspects the surgical instrument include at least one surface portion having a shape that substantially conforms to a corresponding surface portion of the bone. The surgical instrument in such aspects would thus include at least one surface that is substantially a negative of, a mirror image of and/or conforms to at least one surface of the bone.

Other aspects of the patient-specific surgical instrument and methods for making it, including the quantities and types of materials in the resin composition and/or surgical instrument, features of the surgical instrument, and properties of the surgical instrument are discussed above and not reproduced here.

The system thus described may in some aspects be used on-site by a medical professional, such as a surgeon and his/her support staff. The medical professional may, for example, have the system 700 in his/her place of business (e.g., medical office or hospital) during diagnosis of a patient's injury and/or in preparation for surgery on the patient. In an example of a knee replacement procedure, the medical professional (e.g., a medical imaging technician) may obtain image data of at least a portion of a bone corresponding to the knee joint that will require cutting using a suitable surface detection method. The image data is received by the computer system 710, which generates computer-readable instructions to form a surgical instrument (e.g., cutting guide) that is customized to the patient. The computer-readable instructions can then be provided to a machine 720, such as an additive manufacturing machine or a subtractive manufacturing machine, which forms the customized cutting guide based on the computer-readable instructions.

In another aspect, the system 700 may be located separately from that of the location of the medical professional. In an exemplary aspect of a knee replacement procedure, the medical professional may obtain image data of at least a portion of a bone corresponding to the knee joint that will require cutting using a suitable surface detection method.

The medical professional may then send the image data to an off-site facility (e.g., a surgical instrument manufacturing facility) by a suitable method, such as by sending the image data by electronic mail, by Internet file transfer, or by regular mail, etc. The off-site facility receives the image data and automatically or manually inputs the image data into the computer system 710, which generates computer-readable instructions to form a surgical instrument (e.g., cutting guide) that is customized to the patient. The computer-readable instructions can be reviewed and adjusted as necessary, and the computer-readable instructions can then be provided to a machine 720, such as an additive manufacturing machine or a subtractive manufacturing machine, which forms the customized cutting guide based on the computer-readable instructions.

In certain aspects the customized surgical instrument, which includes the resin composition according to aspects described herein, has sufficient strength and/or surface hardness such that no secondary surface enhancements need be performed on the instrument prior to its use on the patient. Exemplary additive manufacturing machines include those discussed above, and are not duplicated here.

Method for Manufacture of a Personalized Surgical Instrument

Figure 8:
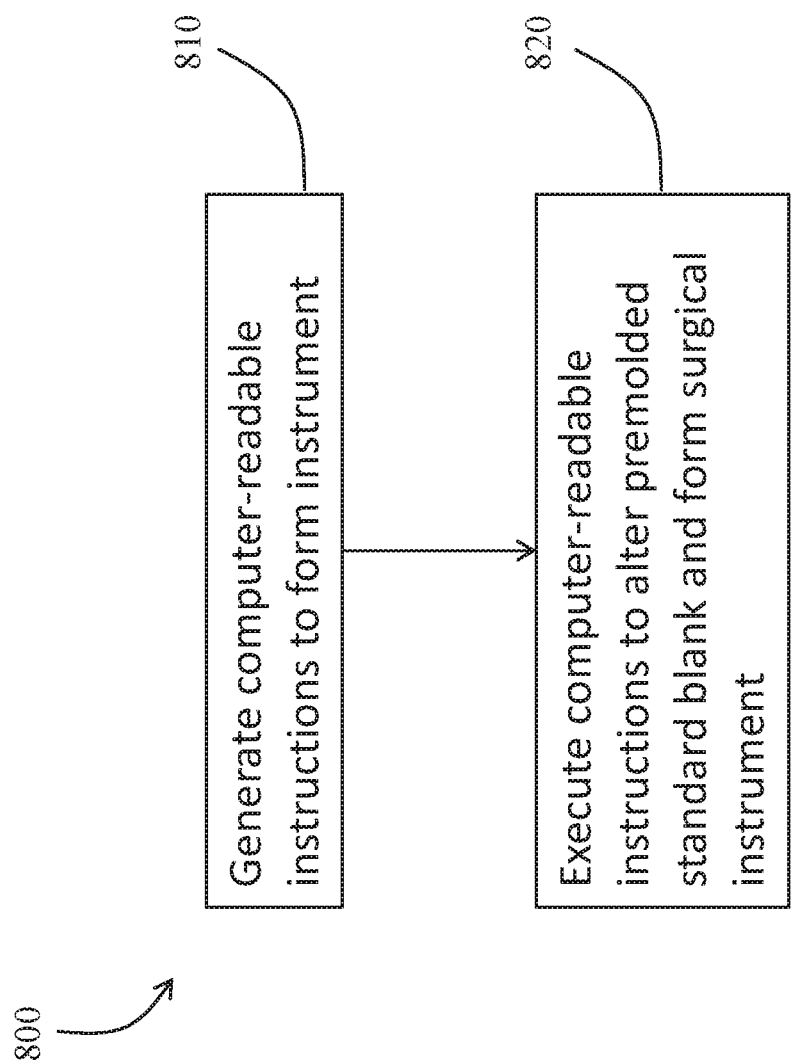
FIG. 8 is a flowchart illustrating a method according to an aspect of the disclosure.

With reference to FIG. 8, aspects of the disclosure further relate to a method for making a patient-specific surgical instrument, such as an orthopedic surgical instrument. The method 800 includes: generating computer-readable instructions to form the surgical instrument based at least in part on image data obtained from at least a portion of a bone corresponding to the joint of the patient, at 810; and executing the computer-readable instructions to alter a premolded standard blank and form the surgical instrument, at 820. The surgical instrument includes at least one surface portion having a shape that substantially conforms to a corresponding surface portion of the bone. The premolded standard blank includes from about 50 wt % to about 90 wt % of a base thermoplastic and from about 10 wt % to about 50 wt % of a filler material. The base thermoplastic includes polyetherimide, polycarbonate, modified polyphenylene ether, polyamide, copolymers of these thermoplastics, and combinations thereof.

The step of generating computer-readable instructions to form the surgical instrument based at least in part on image data obtained from at least a portion of a bone corresponding to the joint of the patient, at 810, may be performed using a computer system such as that described above (see, e.g., computer system 710). The computer system may receive image data of at least a portion of the bone such as that described above with respect to system 700.

The surgical instrument may be formed at step 820 by executing the computer-readable instructions to alter a premolded standard blank. The computer-readable instructions may be executed by a machine such as that described above (e.g., machine 720).

It will be recognized that some operator input and/or interaction may occur at one or both of steps 810 and 820.

The premolded standard blank includes from about 50 wt % to about 90 wt % of a base thermoplastic and from about 10 wt % to about 50 wt % of a filler material. The premolded standard blank may also include up to 20 wt % of a lubricant material such as that described herein.

In some aspects the premolded standard blank is altered by removing material from the premolded standard blank in a subtractive manufacturing process. Thus, a subtractive manufacturing apparatus executes the computer-readable instructions to alter the premolded standard blank and remove material from it.

In other aspects the premolded standard blank is altered by adding material to the premolded standard blank using an additive manufacturing process. Thus, an additive manufacturing apparatus executes the computer-readable instructions to alter the premolded standard blank and add material to it. It will be recognized that in such aspects it may be desirable to select a premolded standard blank that is smaller than the surgical instrument to be formed. A person skilled in the art can select a premolded standard blank of suitable size for a particular surgical instrument to be formed. Exemplary additive manufacturing processes include those discussed above, and are not duplicated here.

Other aspects of relating to the method for making the surgical instrument, including the quantities and types of materials in the premolded standard blank and/or surgical instrument, features of the surgical instrument, and properties of the surgical instrument are discussed above and not reproduced here.

The method thus described is suitable for on-site use by a medical professional, or for use at a location separate from that of the medical professional, as described above with respect to system 700.

Aspects of the disclosure relating to the surgical instruments and methods for making them described herein thus provide substantial benefits over prior surgical instruments which are not disposable (i.e., not single-use instruments) and/or are not customizable to the patient. Surgical instruments according to the present disclosure, which may be prepackaged as sterile (or ready to be sterilized) trays of single-use instruments eases the logistical burden and helps to ensure that medical professionals are using sterile instruments in their best condition (e.g., not dull or bent). Further, the reduction in weight achieved by using thermoplastic-based instruments could result in fewer injuries to hospital personnel, as they would no longer need to move heavy trays full of metal instruments. Thermoplastic-based surgical instruments according to the present disclosure are also substantially less expensive to make than the metal instruments currently in use. In addition, compared to the current plastic patient personalized cutting guides, which lack strength, surgical instruments according to the present disclosure have superior performance due to better strength, stiffness, and wear properties.

Various combinations of elements of this disclosure are encompassed by this disclosure, e.g. combinations of elements from dependent claims that depend upon the same independent claim.

Aspects of the Disclosure

In various aspects, the present disclosure pertains to and includes at least the following aspects.

Aspects of Surgical Instrument, Kit and Method for Making Surgical Instrument

Aspect 1: An orthopedic surgical instrument, comprising:
from about 40 wt % to about 85 wt % of a base thermoplastic selected from the group consisting of polyetherimide, polycarbonate, modified polyphenylene ether, polyamide, copolymers of these thermoplastics, and combinations thereof and
from about 15 wt % to about 60 wt % of a filler material, wherein all materials in the orthopedic surgical instrument are biocompatible.

Aspect 2: The orthopedic surgical instrument according to Aspect 1, wherein the filler material is selected from the group consisting of carbon, ultra-high molecular weight polyethylene, and combinations thereof.

Aspect 3: The orthopedic surgical instrument according to Aspects 1 or 2, wherein the orthopedic surgical instrument further comprises up to 20 wt % of a lubricant material.

Aspect 4: The orthopedic surgical instrument according to Aspect 3, wherein the lubricant material is selected from the group consisting of polytetrafluoroethylene, polyfluoropolyether, hydrocarbon-based synthetic oils, graphite, titanium dioxide, molybdenum disulfide, boron nitride, silicone compounds, and combinations thereof.

Aspect 5: The orthopedic surgical instrument according to Aspect 1, wherein the orthopedic surgical instrument comprises about 60 wt % to about 80 wt % base thermoplastic comprising polyetherimide, polycarbonate or polyamide and about 20 wt % to about 40 wt % filler material comprising carbon.

Aspect 6: The orthopedic surgical instrument according to Aspect 1, wherein the orthopedic surgical instrument comprises about 45 wt % to about 75 wt % base thermoplastic comprising polyetherimide, polycarbonate or polyamide, about 20 wt % to about 40 wt % filler material comprising carbon, and about 5 wt % to about 15 wt % of a lubricant material.

Aspect 7: The orthopedic surgical instrument according to Aspect 1, wherein the orthopedic surgical instrument comprises about 40 wt % to about 60 wt % base thermoplastic and about 40 wt % to about 60 wt % filler material comprising ultra-high molecular weight polyethylene.

Aspect 8: The orthopedic surgical instrument according to any of the previous Aspects, wherein the orthopedic surgical instrument is a single-use instrument.

Aspect 9: The orthopedic surgical instrument according to any of the previous Aspects, wherein the orthopedic surgical instrument is a cutting guide.

Aspect 10: The orthopedic surgical instrument according to Aspect 9, wherein the cutting guide exhibits minimal scratching and no observable debris generation during use.

Aspect 11: The orthopedic surgical instrument according to Aspect 9 or 10, wherein the cutting guide comprises at least one first surface proximate a location to where a cutting implement is adjacent the cutting guide during use, and wherein predominantly more filler material is located on the at least one first surface of the orthopedic surgical instrument than at other surfaces of the orthopedic surgical instrument that are distal to where the cutting implement is adjacent the cutting guide during use.

Aspect 12: The orthopedic surgical instrument according to Aspect 9 or 10, wherein the cutting guide comprises at least one first surface proximate a location to where a cutting implement is adjacent the cutting guide during use, and wherein predominantly more base thermoplastic is located on the at least one first surface of the orthopedic surgical instrument than at other surfaces of the orthopedic surgical instrument that are distal to where the cutting implement is adjacent the cutting guide during use.

Aspect 13: The orthopedic surgical instrument according to Aspect 9 or 10, wherein the orthopedic surgical instrument further comprises up to 20 wt % of a lubricant material, and wherein the cutting guide comprises at least one first surface proximate a location to where a cutting implement is adjacent the cutting guide during use, and wherein predominantly more lubricant material is located on the at least one first surface of the orthopedic surgical instrument than at other surfaces of the orthopedic surgical instrument that are distal to where the cutting implement is adjacent the cutting guide during use.

Aspect 14: The orthopedic surgical instrument according to Aspects 11 to 13, wherein the at least one surface is uncoated.

Aspect 15: The orthopedic surgical instrument according to any of the previous Aspects, wherein the orthopedic surgical instrument is formed in an additive manufacturing process.

Aspect 16: The orthopedic surgical instrument according to any of Aspects 1 to 14, wherein the orthopedic surgical instrument is injection molded.

Aspect 17: The orthopedic surgical instrument according to any of Aspects 1 to 14, wherein the orthopedic surgical instrument is formed from a premolded standard blank in a subtractive manufacturing process.

Aspect 18: An orthopedic surgical kit, comprising:
an orthopedic surgical instrument, the orthopedic surgical instrument comprising
from about 50 wt % to about 90 wt % of a base thermoplastic selected from the group consisting of polyetherimide, polycarbonate, modified polyphenylene ether, polyamide, copolymers of these thermoplastics, and combinations thereof and
from about 10 wt % to about 50 wt % of a filler material, and
a container suitable for sealing the orthopedic surgical instrument therein, wherein all materials in the orthopedic surgical instrument are biocompatible.

Aspect 19: The orthopedic surgical kit according to Aspect 18, wherein the container comprises one or more materials suitable for maintaining sterility of the orthopedic surgical instrument contained therein during transportation or storage thereof.

Aspect 20: The orthopedic surgical kit according to Aspect 19, wherein the one or more materials are selected from the group consisting of high density polyethylene, polyester, polyethylene, polycarbonate, polyurethane, polyethylene terephthalate glycol, polyethylene terephthalate, acrylonitrile-butadiene-styrene, polyvinyl chloride, polystyrene, cellophane, laminates of one or more of these materials, coextruded films including one or more of these materials, and combinations thereof.

Aspect 21: A method for making an orthopedic surgical instrument, comprising:
forming the orthopedic surgical instrument from a resin composition comprising from about 50 wt % to about 90 wt % of a base thermoplastic and from about 10 wt % to about 50 wt % of a filler material,
wherein the base thermoplastic is selected from the group consisting of polyetherimide, polycarbonate, modified polyphenylene ether, polyamide, copolymers of these thermoplastics, and combinations thereof, and wherein all materials in the orthopedic surgical instrument are biocompatible.

Aspect 22: The method according to Aspect 21, wherein the filler material is selected from the group consisting of carbon, ultra-high molecular weight polyethylene, and combinations thereof.

Aspect 23: The method according to Aspect 21 or 22, wherein the resin composition further comprises up to 20 wt % of a lubricant material.

Aspect 24: The method according to Aspect 23, wherein the lubricant material is selected from the group consisting of polytetrafluoroethylene, polyfluoropolyether, hydrocarbon-based synthetic oils, graphite, titanium dioxide, molybdenum disulfide, boron nitride, silicone compounds, and combinations thereof.

Aspect 25: The method according to Aspect 21, wherein the resin composition comprises about 60 wt % to about 80 wt % base thermoplastic comprising polyetherimide, polycarbonate or polyamide and about 20 wt % to about 40 wt % filler material comprising carbon.

Aspect 26: The method according to Aspect 21, wherein the resin composition comprises about 45 wt % to about 75 wt % base thermoplastic comprising polyetherimide, polycarbonate or polyamide, about 20 wt % to about 40 wt % filler material comprising carbon, and about 5 wt % to about 15 wt % of a lubricant material.

Aspect 27: The method according to Aspect 21, wherein the resin composition comprises about 40 wt % to about 60 wt % base thermoplastic and about 40 wt % to about 60 wt % filler material comprising ultra-high molecular weight polyethylene.

Aspect 28: The method according to any of Aspects 21 to 27, wherein forming the orthopedic surgical instrument from the resin composition comprises:
heating the resin composition; and
injection molding the orthopedic surgical instrument from the heated resin composition.

Aspect 29: The method according to any of Aspects 21 to 27, wherein forming the orthopedic surgical instrument from the resin composition comprises:
heating the resin composition; and
forming the orthopedic surgical instrument from the heated resin composition in an additive manufacturing process.

Aspect 30: The method according to any of Aspects 21 to 27, wherein forming the orthopedic surgical instrument from the resin composition comprises:
forming the orthopedic surgical instrument from a premolded standard blank in a subtractive manufacturing process.

Aspect 31: The method according to any of Aspects 21 to 30, wherein the orthopedic surgical instrument is a single-use instrument.

Aspect 32: The method according to any of Aspects 21 to 31, wherein the orthopedic surgical instrument is a cutting guide.

Aspect 33: The method according to Aspect 32, wherein the cutting guide exhibits minimal scratching and no observable debris generation during use.

Aspect 34: The method according to Aspects 32 or 33, wherein forming the orthopedic surgical instrument comprises controlling a temperature of at least one first surface of the orthopedic surgical instrument proximate a location to where a cutting implement is adjacent the cutting guide during use such that predominantly more filler material is located on the at least one first surface of the orthopedic surgical instrument than at other surfaces of the orthopedic surgical instrument that are distal to where the cutting implement is adjacent the cutting guide during use.

Aspect 35: The method according to Aspects 32 or 33, wherein forming the orthopedic surgical instrument comprises controlling a temperature of at least one first surface of the orthopedic surgical instrument proximate a location to where a cutting implement is adjacent the cutting guide during use such that predominantly more base thermoplastic is located on the at least one first surface of the orthopedic surgical instrument than at other surfaces of the orthopedic surgical instrument that are distal to where the cutting implement is adjacent the cutting guide during use.

Aspect 36: The method according to Aspects 32 or 33, wherein the orthopedic surgical instrument further comprises up to 20 wt % of a lubricant material, and wherein forming the orthopedic surgical instrument comprises controlling a temperature of at least one first surface of the orthopedic surgical instrument proximate a location to where a cutting implement is adjacent the cutting guide during use such that predominantly more lubricant material is located on the at least one first surface of the orthopedic surgical instrument than at other surfaces of the orthopedic surgical instrument that are distal to where the cutting implement is adjacent the cutting guide during use.

Aspect 37: The method according to Aspects 34 to 36, wherein no secondary surface enhancements are performed on the at least one surface.

Aspect 38: The method according to any of Aspects 21 to 37, further comprising sterilizing the orthopedic surgical instrument.

Aspect 39: The method according to any of Aspects 21 to 38 further comprising packaging the orthopedic surgical instrument.

Aspects of Method for Making Customized Instrument and Patient-Specific Instrument Aspect 1: A method for making a customized orthopedic surgical instrument for use in repairing a joint of a patient, the method comprising:

obtaining image data associated with at least a portion of a bone corresponding to the joint of the patient;

generating computer-readable instructions to form a patient-specific orthopedic surgical instrument based at least in part on the image data;

forming the patient-specific orthopedic surgical instrument based on the computer-readable instructions, the patient-specific orthopedic surgical instrument comprising a resin composition comprising:

from about 50 wt % to about 90 wt % of a base thermoplastic selected from the group consisting of polyetherimide, polycarbonate, modified polyphenylene ether, polyamide, copolymers of these thermoplastics, and combinations thereof; and from about 10 wt % to about 50 wt % of a filler material, wherein the orthopedic surgical instrument includes at least one surface portion having a shape that substantially conforms to a corresponding surface portion of the bone, and wherein all materials in the orthopedic surgical instrument are biocompatible.

Aspect 2: The method according to Aspect 1, wherein the orthopedic surgical instrument is a cutting guide.

Aspect 3: The method according to Aspect 1 or 2, wherein forming the patient-specific orthopedic surgical instrument comprises injection molding the instrument from the resin composition.

Aspect 4: The method according to Aspect 1 or 2, wherein forming the patient-specific orthopedic surgical instrument comprises forming the instrument from the resin composition in an additive manufacturing process.

Aspect 5: The method according to Aspect 1 or 2, wherein forming the patient-specific orthopedic surgical instrument comprises forming the instrument from a premolded standard blank in a subtractive or additive manufacturing process, wherein the premolded standard blank comprises the resin composition.

Aspect 6: The method according to any of the previous Aspects, wherein no secondary surface enhancements are performed on the patient-specific orthopedic surgical instrument.

Aspect 7: The method according to any of the previous Aspects, further comprising sterilizing the patient-specific surgical instrument.

Aspect 8: The method according to any of the previous Aspects, further comprising packaging the patient-specific orthopedic surgical instrument into a package suitable for maintaining sterility of the patient-specific surgical instrument during transportation or storage thereof.

Aspect 9: The method according to Aspect 8, wherein the package comprises a material selected from the group consisting of high density polyethylene, polyester, polyethylene, polycarbonate, polyurethane, polyethylene terephthalate glycol, polyethylene terephthalate, acrylonitrile-butadiene-styrene, polyvinyl chloride, polystyrene, cellophane, laminates of one or more of these materials, coextruded films including one or more of these materials, and combinations thereof.

Aspect 10: The method according to any of the previous Aspects, wherein the filler material is selected from the group consisting of carbon, ultra-high molecular weight polyethylene, and combinations thereof.

Aspect 11: The method according to any of the previous Aspects, wherein the resin composition further comprises up to 20 wt % of a lubricant material.

Aspect 12: The method according to Aspect 11, wherein the lubricant material is selected from the group consisting of polytetrafluoroethylene, polyfluoropolyether, hydrocarbon-based synthetic oils, graphite, titanium dioxide, molybdenum disulfide, boron nitride, silicone compounds, and combinations thereof.

Aspect 13: The method according to Aspect 1, wherein the resin composition comprises about 60 wt % to about 80 wt % base thermoplastic comprising polyetherimide, polycarbonate or polyamide and about 20 wt % to about 40 wt % filler material comprising carbon.

Aspect 14: The method according to Aspect 11, wherein the resin composition comprises about 45 wt % to about 75 wt % base thermoplastic comprising polyetherimide, polycarbonate or polyamide, about 20 wt % to about 40 wt % filler material comprising carbon, and about 5 wt % to about 15 wt % of a lubricant material.

Aspect 15: The method according to Aspect 1, wherein the resin composition comprises about 40 wt % to about 60 wt % base thermoplastic and about 40 wt % to about 60 wt % filler material comprising ultra-high molecular weight polyethylene.

Aspect 16: The method according to any of the previous Aspects, wherein the patient-specific orthopedic surgical instrument is a single-use instrument.

Aspect 17: The method according to any of the previous Aspects, wherein the patient-specific orthopedic surgical instrument exhibits minimal scratching and no observable debris generation during use.

Aspect 18: The method according to Aspect 2, wherein forming the patient-specific orthopedic surgical instrument comprises controlling a temperature of at least one first surface of the patient-specific orthopedic surgical instrument proximate a location to where a cutting implement is adjacent the cutting guide during use such that predominantly more filler material is located on the at least one first surface of the patient-specific orthopedic surgical instrument than at other surfaces of the patient-specific orthopedic surgical instrument that are distal to where the cutting implement is adjacent the cutting guide during use.

Aspect 19: The method according to Aspect 2, wherein forming the patient-specific orthopedic surgical instrument comprises controlling a temperature of at least one first surface of the patient-specific orthopedic surgical instrument proximate a location to where a cutting implement is adjacent the cutting guide during use such that predominantly more base thermoplastic is located on the at least one first surface of the patient-specific orthopedic surgical instrument than at other surfaces of the patient-specific orthopedic surgical instrument that are distal to where the cutting implement is adjacent the cutting guide during use.

Aspect 20: The method according to Aspect 2, wherein the patient-specific orthopedic surgical instrument further comprises up to 20 wt % of a lubricant material, and wherein forming the patient-specific orthopedic surgical instrument comprises controlling a temperature of at least one first surface of the patient-specific orthopedic surgical instrument proximate a location to where a cutting implement is adjacent the cutting guide during use such that predominantly more lubricant material is located on the at least one first surface of the patient-specific orthopedic surgical instrument than at other surfaces of the patient-specific orthopedic surgical instrument that are distal to where the cutting implement is adjacent the cutting guide during use.

Aspect 21: A patient-specific orthopedic surgical instrument for use in repairing a joint of a patient, comprising:
from about 50 wt % to about 90 wt % of a base thermoplastic selected from the group consisting of polyetherimide, polycarbonate, modified polyphenylene ether, polyamide, copolymers of these thermoplastics, and combinations thereof; and
from about 10 wt % to about 50 wt % of a filler material, wherein the patient-specific orthopedic surgical instrument includes at least one surface portion having a shape that substantially conforms to a corresponding surface portion of a bone corresponding to the joint of the patient, and wherein all materials in the patient-specific orthopedic surgical instrument are biocompatible.

Aspect 22: The patient-specific orthopedic surgical instrument according to Aspect 21, wherein the orthopedic surgical instrument is a cutting guide.

Aspect 23: The patient-specific orthopedic surgical instrument according to Aspect 21 or 22, wherein the orthopedic surgical instrument is injection-molded.

Aspect 24: The patient-specific orthopedic surgical instrument according to Aspect 21 or 22, wherein the orthopedic surgical instrument is formed using an additive manufacturing process.

Aspect 25: The patient-specific orthopedic surgical instrument according to Aspect 21 or 22, wherein the orthopedic surgical instrument is formed from a premolded standard blank using a subtractive or additive manufacturing process.

Aspect 26: The patient-specific orthopedic surgical instrument according to any of Aspects 21 to 25, wherein the patient-specific orthopedic surgical instrument is uncoated.

Aspect 27: The patient-specific orthopedic surgical instrument according to any of Aspects 21 to 26, wherein the filler material is selected from the group consisting of carbon, ultra-high molecular weight polyethylene, and combinations thereof.

Aspect 28: The patient-specific orthopedic surgical instrument according to any of Aspects 21 to 27, wherein the patient-specific orthopedic surgical instrument further comprises up to 20 wt % of a lubricant material.

Aspect 29: The patient-specific orthopedic surgical instrument according to Aspect 28, wherein the lubricant material is selected from the group consisting of polytetrafluoroethylene, polyfluoropolyether, hydrocarbon-based synthetic oils, graphite, titanium dioxide, molybdenum disulfide, boron nitride, silicone compounds, and combinations thereof.

Aspect 30: The patient-specific orthopedic surgical instrument according to Aspect 21, wherein the orthopedic surgical instrument comprises about 60 wt % to about 80 wt % base thermoplastic comprising polyetherimide, polycarbonate or polyamide and about 20 wt % to about 40 wt % filler material comprising carbon.

Aspect 31: The patient-specific orthopedic surgical instrument according to Aspect 21, wherein the orthopedic surgical instrument comprises about 45 wt % to about 75 wt % base thermoplastic comprising polyetherimide, polycarbonate or polyamide, about 20 wt % to about 40 wt % filler material comprising carbon, and about 5 wt % to about 15 wt % of a lubricant material.

Aspect 32: The patient-specific orthopedic surgical instrument according to Aspect 21, wherein the patient-specific orthopedic surgical instrument comprises about 40 wt % to about 60 wt % base thermoplastic and about 40 wt % to about 60 wt % filler material comprising ultra-high molecular weight polyethylene.

Aspect 33: The patient-specific orthopedic surgical instrument according to any of Aspects 21 to 32, wherein the patient-specific orthopedic surgical instrument is a single-use instrument.

Aspect 34: The patient-specific orthopedic surgical instrument according to any of Aspects 21 to 33, wherein the cutting guide exhibits minimal scratching and no observable debris generation during use.

Aspect 35: The patient-specific orthopedic surgical instrument according to Aspect 22, wherein the cutting guide comprises at least one first surface proximate a location to where a cutting implement is adjacent the cutting guide during use, and wherein predominantly more filler material is located on the at least one first surface of the patient-specific orthopedic surgical instrument than at other surfaces of the patient-specific orthopedic surgical instrument that are distal to where the cutting implement is adjacent the cutting guide during use.

Aspect 36: The patient-specific orthopedic surgical instrument according to Aspect 22, wherein the cutting guide comprises at least one first surface proximate a location to where a cutting implement is adjacent the cutting guide during use, and wherein predominantly more base thermoplastic is located on the at least one first surface of the patient-specific orthopedic surgical instrument than at other surfaces of the patient-specific orthopedic surgical instrument that are distal to where the cutting implement is adjacent the cutting guide during use.

Aspect 37: The patient-specific orthopedic surgical instrument according to Aspect 22, wherein the patient-specific orthopedic surgical instrument further comprises up to 20 wt % of a lubricant material, and wherein the cutting guide comprises at least one first surface proximate a location to where a cutting implement is adjacent the cutting guide during use, and wherein predominantly more lubricant material is located on the at least one first surface of the patient-specific orthopedic surgical instrument than at other surfaces of the patient-specific orthopedic surgical instrument that are distal to where the cutting implement is adjacent the cutting guide during use.

Aspects of System and Method for On-Site Manufacture of Instrument

Aspect 1: A system for making a customized orthopedic surgical instrument for use in repairing a joint of a patient, the system comprising:
a computer system for generating computer-readable instructions to form a patient-specific orthopedic surgical instrument based at least in part on image data obtained from at least a portion of a bone corresponding to the joint of the patient; and a machine for forming a patient-specific orthopedic surgical instrument from the computer-readable instructions, the patient-specific orthopedic surgical instrument comprising a resin composition comprising:
from about 50 wt % to about 90 wt % of a base thermoplastic selected from the group consisting of polyetherimide, polycarbonate, modified polyphenylene ether, polyamide, copolymers of these thermoplastics, and combinations thereof and
from about 10 wt % to about 50 wt % of a filler material, wherein the patient-specific orthopedic surgical instrument includes at least one surface portion having a shape that substantially conforms to a corresponding surface portion of the bone, and wherein all materials in the patient-specific orthopedic surgical instrument are biocompatible.

Aspect 2: The system according to Aspect 1, wherein the machine comprises an additive manufacturing apparatus.

Aspect 3: The system according to Aspect 1, wherein the machine comprises a subtractive manufacturing apparatus, and the patient-specific orthopedic surgical instrument is formed from a premolded standard blank, the premolded standard blank comprising the resin composition.

Aspect 4: The system according to any of the previous Aspects, wherein the filler material is selected from the group consisting of carbon, ultra-high molecular weight polyethylene, and combinations thereof.

Aspect 5: The system according to any of the previous Aspects, wherein the resin composition further comprises up to 20 wt % of a lubricant material.

Aspect 6: The system according to Aspect 5, wherein the lubricant material is selected from the group consisting of polytetrafluoroethylene, polyfluoropolyether, hydrocarbon-based synthetic oils, graphite, titanium dioxide, molybdenum disulfide, boron nitride, silicone compounds, and combinations thereof.

Aspect 7: The system according to Aspect 1, wherein the resin composition comprises about 60 wt % to about 80 wt % base thermoplastic comprising polyetherimide, polycarbonate or polyamide and about 20 wt % to about 40 wt % filler material comprising carbon.

Aspect 8: The system according to Aspect 1, wherein the resin composition comprises about 45 wt % to about 75 wt % base thermoplastic comprising polyetherimide, polycarbonate or polyamide, about 20 wt % to about 40 wt % filler material comprising carbon, and about 5 wt % to about 15 wt % of a lubricant material.

Aspect 9: The system according to Aspect 1, wherein the resin composition comprises about 40 wt % to about 60 wt % base thermoplastic and about 40 wt % to about 60 wt % filler material comprising ultra-high molecular weight polyethylene.

Aspect 10: The system according to any of the previous Aspects, wherein the patient-specific orthopedic surgical instrument is a single-use instrument.

Aspect 11: The system according to any of the previous Aspects, wherein the patient-specific orthopedic surgical instrument is a cutting guide.

Aspect 12: The system according to any of the previous Aspects, wherein the patient-specific orthopedic surgical instrument exhibits minimal scratching and no observable debris generation during use.

Aspect 13: A method for making a patient-specific orthopedic surgical instrument for use in repairing a joint of a patient, the method comprising:
generating computer-readable instructions to form the orthopedic surgical instrument based at least in part on image data obtained from at least a portion of a bone corresponding to the joint of the patient; and
executing the computer-readable instructions to alter a premolded standard blank and form the orthopedic surgical instrument, wherein the orthopedic surgical instrument includes at least one surface portion having a shape that substantially conforms to a corresponding surface portion of the bone,
wherein the premolded standard blank comprises
from about 50 wt % to about 90 wt % of a base thermoplastic selected from the group consisting of polyetherimide, polycarbonate, modified polyphenylene ether, polyamide, copolymers of these thermoplastics, and combinations thereof, and
from about 10 wt % to about 50 wt % of a filler material.

Aspect 14: The method according to Aspect 13, wherein the premolded standard blank is altered by removing material from the premolded standard blank in a subtractive manufacturing process.

Aspect 15: The method according to Aspect 13, wherein the premolded standard blank is altered by adding material to the premolded standard blank using an additive manufacturing process.

Aspect 16: The method according to any of Aspects 13 to 15, wherein the filler material is selected from the group consisting of carbon, ultra-high molecular weight polyethylene, and combinations thereof.

Aspect 17: The method according to any of Aspects 13 to 16, wherein the premolded standard blank further comprises up to 20 wt % of a lubricant material.

Aspect 18: The method according to Aspect 17, wherein the lubricant material is selected from the group consisting of polytetrafluoroethylene, polyfluoropolyether, hydrocarbon-based synthetic oils, graphite, titanium dioxide, molybdenum disulfide, boron nitride, silicone compounds, and combinations thereof.

Aspect 19: The method according to Aspect 13, wherein the premolded standard blank comprises about 60 wt % to about 80 wt % base thermoplastic comprising polyetherimide, polycarbonate or polyamide and about 20 wt % to about 40 wt % filler material comprising carbon.

Aspect 20: The method according to Aspect 13, wherein the resin composition comprises about 45 wt % to about 75 wt % base thermoplastic comprising polyetherimide, polycarbonate or polyamide, about 20 wt % to about 40 wt % filler material comprising carbon, and about 5 wt % to about 15 wt % of a lubricant material.

Aspect 21: The method according to Aspect 13, wherein the premolded standard blank comprises about 40 wt % to about 60 wt % base thermoplastic and about 40 wt % to about 60 wt % filler material comprising ultra-high molecular weight polyethylene.

Aspect 22: The method according to any of Aspects 13 to 21, wherein the orthopedic surgical instrument is a single-use instrument.

Aspect 23: The method according to any of Aspects 13 to 22, wherein the orthopedic surgical instrument is a cutting guide.

Aspect 24: The method according to any of Aspects 13 to 23, wherein the orthopedic surgical instrument exhibits minimal scratching and no observable debris generation during use.

Aspect 25: The method according to any of Aspects 13 to 24, wherein no secondary surface enhancements are performed on the orthopedic surgical instrument.

Aspect 26: The method according to any of Aspects 13 to 25, further comprising sterilizing the orthopedic surgical instrument.

Aspect 27: The method according to any of Aspects 13 to 26 further comprising packaging the orthopedic surgical instrument.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Sample cutting guides were formed from injection-molded (except where indicated) plaques of the following materials and tested by passing an oscillating saw blade alongside, with the observed results:

| No. | Material Tested | Observations |
|---|---|---|
| C1 | Polycarbonate | Extensive scratching; no significant debris generation observed |
| C2 | Polycarbonate Exatec ™ E900 | Extensive scratching; no significant debris generation observed |
| C3 | Polyetherimide | Extensive scratching; no significant debris generation observed |
| C4 | Nylon 6,6 | Extensive scratching; no significant debris generation observed |
| C5 | Polyetheretherketone/PTFE/ carbon fiber (70/15/15) | Extensive scratching; no significant debris generation observed |
| C6 | Nylon 12* | Extensive debris; damage to part surface |
| Ex1 | Polyetherimide/carbon fiber (70/30) | Minimal scratching, no debris generation observed |
| Ex2 | Nylon 6,6/carbon fiber (60/40) | Minimal scratching, no debris generation observed |

All samples were 100% of the indicated material unless otherwise noted
*Plaque was additive-manufactured The examples demonstrated that several known thermoplastic materials, without a filler, are unsuitable for use as surgical instruments due to extensive scratching. See Comparative Examples C1-C4 and C6. This was the case even for a polycarbonate material with a proven abrasion-resistant coating (Example C2, Exatec™ E900, available from SABIC). Even a partially filled polyetheretherketone material (Example C5) exhibited extensive scratching and was unsuitable. In contrast, Examples Ex1 and Ex2 according to aspects of the present disclosure exhibited minimal scratching and no observed debris generation, and would be suitable for use in a surgical instrument without any further treatment processes (i.e., secondary surface enhancements).

Methods and systems described herein can be machine or computer-implemented at least in part. Some methods and systems can include a computer-readable medium or machine-readable medium encoded with instructions operable to configure an electronic device to perform processes as described herein. Implementation of such methods and systems can include code, such as microcode, assembly language code, a higher-level language code, or the like. Such code can include computer readable instructions for performing various methods and/or processes. The code may form portions of computer program products. Further, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

That which is claimed is:

1. An orthopedic surgical instrument, comprising:
    from about 40 wt % to about 84 wt % of a base thermoplastic selected from the group consisting of polyetherimide, polycarbonate, modified polyphenylene ether, polyamide, copolymers of these thermoplastics, and combinations thereof;
    from about 15 wt % to about 40 wt % of a filler material; and
    from about 1 wt % to about 20 wt % of a lubricant material,
    wherein all materials in the orthopedic surgical instrument are biocompatible.

2. The orthopedic surgical instrument according to claim 1, wherein the filler material is selected from the group consisting of carbon, ultra-high molecular weight polyethylene, and combinations thereof.

3. The orthopedic surgical instrument according to claim 1, wherein the lubricant material is selected from the group consisting of polytetrafluoroethylene, polyfluoropolyether, hydrocarbon-based synthetic oils, graphite, titanium dioxide, molybdenum disulfide, boron nitride, silicone compounds, and combinations thereof.

4. The orthopedic surgical instrument according to claim 1, wherein the base thermoplastic comprises polyetherimide, polycarbonate or polyamide and the filler material comprises carbon.

5. The orthopedic surgical instrument according to claim 1, wherein the orthopedic surgical instrument comprises about 45 wt % to about 75 wt % base thermoplastic comprising polyetherimide, polycarbonate or polyamide, about 20 wt % to about 40 wt % filler material comprising carbon, and about 5 wt % to about 15 wt % lubricant material.

6. The orthopedic surgical instrument according to claim 1, wherein the orthopedic surgical instrument is a single-use instrument.

7. The orthopedic surgical instrument according to claim 1, wherein the orthopedic surgical instrument is a cutting guide.

8. The orthopedic surgical instrument according to claim 7, wherein the cutting guide exhibits minimal scratching and no observable debris generation during use.

9. The orthopedic surgical instrument according to claim 7, wherein the cutting guide comprises at least one first surface proximate a location to where a cutting implement is adjacent the cutting guide during use, wherein the at least one surface is integral with the cutting guide, and wherein predominantly more filler material is located on the at least one first surface of the orthopedic surgical instrument than at other surfaces of the orthopedic surgical instrument that are distal to where the cutting implement is adjacent the cutting guide during use.

10. The orthopedic surgical instrument according to claim 7, wherein the cutting guide comprises at least one first surface proximate a location to where a cutting implement is adjacent the cutting guide during use, wherein the at least one surface is integral with the cutting guide, and wherein predominantly more base thermoplastic is located on the at least one first surface of the orthopedic surgical instrument than at other surfaces of the orthopedic surgical instrument that are distal to where the cutting implement is adjacent the cutting guide during use.

11. The orthopedic surgical instrument according to claim 7, wherein the cutting guide comprises at least one first surface proximate a location to where a cutting implement is adjacent the cutting guide during use, wherein the at least one surface is integral with the cutting guide, and wherein predominantly more lubricant material is located on the at least one first surface of the orthopedic surgical instrument than at other surfaces of the orthopedic surgical instrument that are distal to where the cutting implement is adjacent the cutting guide during use.

12. The orthopedic surgical instrument according to claim 9, wherein the at least one first surface is uncoated.

13. The orthopedic surgical instrument according to claim 1, wherein the orthopedic surgical instrument is formed in an additive manufacturing process.

14. The orthopedic surgical instrument according to claim 1, wherein the orthopedic surgical instrument is injection molded.

15. The orthopedic surgical instrument according to claim 1, wherein the orthopedic surgical instrument is formed from a premolded standard blank in a subtractive manufacturing process.

16. An orthopedic surgical kit, comprising:
an orthopedic surgical instrument, the orthopedic surgical instrument comprising
from about 50 wt % to about 89 wt % of a base thermoplastic selected from the group consisting of polyetherimide, polycarbonate, modified polyphenylene ether, polyamide, copolymers of these thermoplastics, and combinations thereof;
from about 10 wt % to about 50 wt % of a filler material; and
from about 1 wt % to about 20 wt % of a lubricant material, and
a container suitable for sealing the orthopedic surgical instrument therein, wherein all materials in the orthopedic surgical instrument are biocompatible.

17. The orthopedic surgical kit according to claim 16, wherein the container comprises one or more materials suitable for maintaining sterility of the orthopedic surgical instrument contained therein during transportation or storage thereof.

18. The orthopedic surgical kit according to claim 17, wherein the one or more materials are selected from the group consisting of high density polyethylene, polyester, polyethylene, polycarbonate, polyurethane, polyethylene terephthalate glycol, polyethylene terephthalate, acrylonitrile-butadiene-styrene, polyvinyl chloride, polystyrene, cellophane, laminates of one or more of these materials, coextruded films including one or more of these materials, and combinations thereof.

* * * * *